United States Patent [19]

Coates et al.

[11] Patent Number: 6,010,643
[45] Date of Patent: *Jan. 4, 2000

[54] CHOLESTERIC POLYMER NETWORK

[75] Inventors: David Coates, Merley; Alison Linda May, Corfe Mullen, both of United Kingdom

[73] Assignee: Merck Patent Gesellschaft mit beschrankter Haftung, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/836,914

[22] PCT Filed: Nov. 22, 1995

[86] PCT No.: PCT/EP95/04587

§ 371 Date: May 23, 1997

§ 102(e) Date: May 23, 1997

[87] PCT Pub. No.: WO96/17901

PCT Pub. Date: Jun. 13, 1996

[30] Foreign Application Priority Data

Dec. 3, 1994 [EP] European Pat. Off. ............... 94119101

[51] Int. Cl.[7] .......................... C09K 19/30; C09K 19/52; C09K 19/12; C09K 19/20

[52] U.S. Cl. .................. 252/299.63; 252/299.01; 252/299.66; 252/299.67; 252/299.65; 252/299.61

[58] Field of Search ......................... 252/299.01, 299.63, 252/299.66, 299.65, 299.67, 299.61

[56] References Cited

U.S. PATENT DOCUMENTS

| | | | |
|---|---|---|---|
| 4,784,793 | 11/1988 | Coates et al. ....................... | 252/299.62 |
| 4,983,479 | 1/1991 | Broer et al. .............................. | 430/20 |
| 5,518,652 | 5/1996 | Parri et al. ......................... | 252/299.01 |
| 5,705,093 | 1/1998 | Coates et al. ...................... | 252/299.01 |
| 5,746,940 | 5/1998 | Coates et al. ............................... | 252/1 |

FOREIGN PATENT DOCUMENTS 501563  9/1992  European Pat. Off. .

OTHER PUBLICATIONS

Chem. Abs. 9588, Oct. 1964.

*Primary Examiner*—C. H. Kelly
*Attorney, Agent, or Firm*—Millen, White, Zelano, & Branigan, P.C.

[57] ABSTRACT

The invention relates to a liquid material in the form of cholesteric polymer network, wherein the polymerized material is obtainable by copolymerization of a compound (a) having at least two polymerizable functional groups and a chiral polymerizable compound (b), which is a terpinoid and to novel polymerizable terpinoids.

24 Claims, No Drawings

CHOLESTERIC POLYMER NETWORK

The invention relates to a liquid crystalline material in the form of cholesteric polymer network, wherein the polymerized material is obtainable by copolymerization of a compound (a) having at least two polymerizable functional groups and a chiral polymerizable compound (b), characterized in that (b) is a terpenoid.

In European Patent Application EP 451 905 a liquid crystalline material in the form of an anisotropic gel comprising a polymerized liquid crystalline material is disclosed and a low-molecular nematic liquid crystalline material.

The European patent application EP 0 399 279 discloses erasable, laser-readible recording elements based on ferro-electric liquid crystalline polymers including terpenoid derivatives.

The mesogenic core of these terpenoid derivatives is linked to a polymer group with a long-chained spacer.

There is no hint to cholesteric polymer networks nor to compounds with short-chained spacers.

In accordance with the invention, a liquid crystalline material as described in the opening paragraph is obtained, wherein the polymerized material is obtainable by copolymerization of a compound (a) having at least two polymerizable functional groups and a chiral polymerizable compound (b), characterized in that (b) is a terpenoid.

Preferred embodiments of the invention are:

a) A liquid crystalline material wherein material b) is a polymerizable material comprising a structure element of the formula 1:

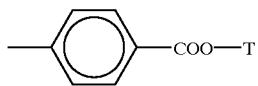

(1)

in which T is a terpenoid radical.

b) A liquid crystalline material wherein the material (b) is obtainable from a chiral, polymerizable compound of the formula I $$R^1\text{-}(P)_u\text{-}X\text{-}(MG^1\text{-}COO)_s\text{-}T \quad\quad I$$

wherein

T is a terpenoid radical $R^1$ $CH_2=CW-COO-$,

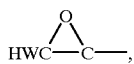

$HWN-$, $CH_2=CH-$, $CH_2=CH-O-$ or $HS-CH_2-(CH_2)_m-COO-$ with W being H, Cl or alkyl with 1–5 C atoms and m being 1–7, P is alkylene with up to 12 C atoms, it being also possible for one or more non adjacent $CH_2$ groups to be replaced by $-O-$, X is $-O-$, $-S-$, $-COO-$, $-OCO-$ or a single bond, $MG^1$ is an aromatic ring system or a mesogenic group comprising two or more ring systems optionally linked by bridging groups, s is 1 or 1, and u is 0 or 1.

c) A liquid crystalline material wherein the terpenoid radical is selected from menthyl, neomenthyl, isopinocampheyl, isolongifolyl, fenchyl, corveyl, myrthenyl, nopyl, citronellyl, dihydrocitronellyl.

d) A liquid crystalline material wherein compound (a) is a bisacrylate of formula IIa

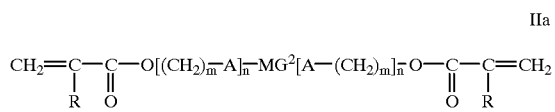

IIa wherein

R is H, $CH_3$ or Cl

A is $-O-$, $-CO-O-$, $-O-CO-$ or a single bond n and m are integers between 0 and 20, $MG^2$ has the meaning given for $MG^1$, in particular selected from

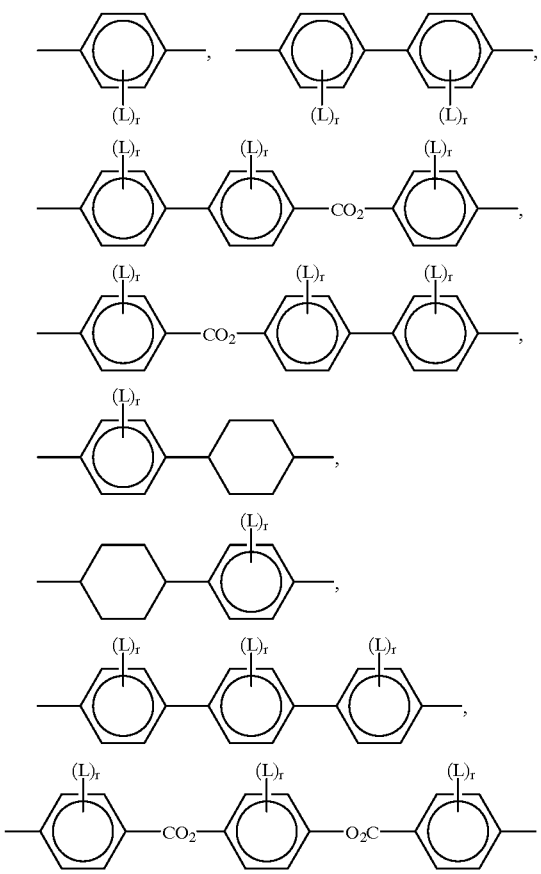

with L being $CH_3$, $-COCH_3$, $-CN$, F or Cl and r being 0, 1 or 2.

e) A liquid crystalline material wherein the polymerizable material comprises at least one achiral compound having one polymerizable functional group, in particular a compound of formula III $$R^2\text{-}(P)_u\text{-}X\text{-}MG^3\text{-}R^3 \quad\quad III$$

in which P, X and u have the meaning given for formula I $R^2$ has the meaning given for $R^1$ $MG^3$ has the meaning given for $MG^1$, and $R^3$ is an optionally halogenated alkyl radical with up to 15 C atoms, it being possible for one or more $CH_2$ groups in these radicals to be replaced by —O—, —S—, —SO—, —OCO—, —COO— or —O—CO—O— in such a manner that oxygen atoms are not linked directly to one another.

f) A liquid crystalline material which is obtainable by copolymerization of at least one polymerizable compound having a short chain spacer group.

Another aspect of the invention is copolymerizable precursor materials comprising at least one bifunctional reactive achiral compound of formula II $$R^4\text{-}(P)_u\text{MG}^2\text{-}X\text{-}(P)_u\text{-}R^4 \qquad \text{II}$$

wherein P, X and u have the meaning given for formula I and $R^4$ has the meaning given for $R^1$, and at least one mono reactive chiral compound of formula I, in particular in which $R^1$ and $R^4$ are independently acrylate radicals of formula

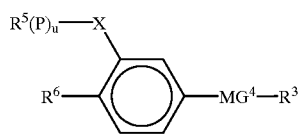

wherein W has the meaning given or in which $R^1$ and $R^4$ are vinylether radicals of formula $CH_2=CH—O—$.

g) Preferred embodiments of this aspect of the invention are copolymerizable precursor materials comprising at least one chiral polymerizable compound of formula I and at least two achiral polymerizable compounds of formula III, wherein at least one compound of formula III has a short chain spacer group and one compound of formula III has a long chain spacer group, in order to suppress smectic phases.

h) Copolymerizable precursor materials comprising at least one chiral compound of formula I and at least one achiral polymerizable compound of formula IV

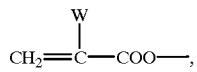

IV

P, X, $R^3$ and u have the meaning given, $R^5$ has the meaning given for $R^1$, $MG^4$ has the meaning given for $MG^1$, and $R^6$ has the meaning given for $R^3$.

Another aspect of the invention is:

reactive chiral compounds of formula I in which at least one aromatic ring is substituted by fluorine; reactive chiral compounds of formula I in which $R^1$ is $CH_2=CH—CO_2—$, X is O, and P is a short-chain spacer of formula —$(CH_2)_k$— with k being an integer between 2 and 10;

reactive chiral compounds of formula I1

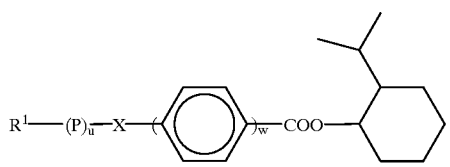

in which $R^1$, P, X and u have the meaning given, and W is 1, 2 or 3, and reactive chiral compounds of formula I2

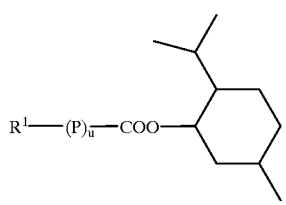

in which $R^1$, P and u have the meaning given.

The inventive compositions comprise as a rule 0.4 to 10%, in particular 1 to 5% of a photoinitiator for example a Darocure® or Irgacure® photoinitiator and 50 to 500 ppm, in particular 100 to 300 ppm of an inhibitior, for example 4-methoxyphenol.

Formula I covers chiral liquid crystalline compounds having no rings (s=o) of formulae Ia and Ib $R^1$-X-T     Ia $R^1$-P-X-T     Ib Formula I covers compounds with one ring of formulae Ic and Id:

$R^1$-X-Phe-COO-T     Ic $R^1$-P-X-Phe-COO-T     Id

Formula I covers chiral reactive liquid crystalline compounds with 2 rings of formulae Ie to I $R^1$-P-X-Phe'-Z-Phe-COO-T     Ie $R^1$-P-X-Phe'-Z-Pyd-COO-T     If $R^1$-P-X-Phe'-Z-Pyr-COO-T     Ig $R^1$-P-X-Nap'-Z-Phe'-COO-T     Ih $R^1$-P-X-Nap-Z-Pyd-COO-T     Ii $R^1$-P-X-Nap-Z-Pyr-COO-T     Ij and compounds with 3 rings of formulae Ik to Iq $R^1$-P-X-Phe'-Z-Phe"-Phe"-COO-T     Ik $R^1$-P-X-Phe'-Z-Pyd-Phe"-COO-T     Il $R^1$-P-X-Phe'-Z-Pyr-Phe"-COO-T     Im $R^1$-P-X-Phe'-Z-Phe"-Pyd-COO-T     In $R^1$-P-X-Phe'-Z-Phe"-Pyr-COO-T     Io $R^1$-P-X-Nap'-Z-Phe"-Phe-COO-T     Ip R¹-P-X-Nap'-Z-Phe'-Pyr-COO-T    Iq Wherein R⁴, R⁵, P, X and C* have the meaning given, Pyd denotes pyrimidine-2,5-diyl and Pyr denotes pyridine-2,5-diyl.

Z denotes —CO—O—, —O—CO—, —CH₂O—, —OCH₂—, —CH₂CH₂—, —C≡C— or a single bond.

In the compounds of formulae Ia–Iq, Phe' denotes a 1,4-phenylene group

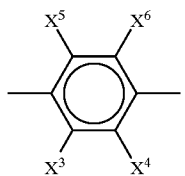

wherein $X^3$–$X^6$ denote independently from each other H or halogen or methyl.

In the compounds of formulae Ia–Iq, Phe" is a 1,4-phenylene group, which is unsubstituted or mono- or polysubstituted by CN or halogen, and in formulae Ig–Ij and Iu–Iy, Nap' is a naphthaline-2,6-diyl group

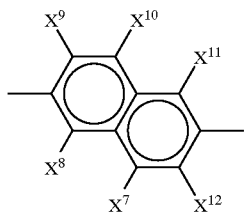

which is unsubstituted or wherein up to 4 of $X^7$–$X^{12}$ are independently from each other halogen while the other denote H.

The compounds of formulae Ia–Ij are preferred. Especially preferred are the compounds of formulae Ia–Ie, in particular the compounds of formulae Ib, Id, and Ie.

In the compounds of formulae Ia–Iq R¹ is CH₂=CW—COO—, CH₂=CH—O—,

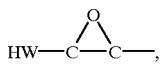

HWN—, HS—CH₂—(CH₂)ₘ—COO— with W being H, Cl or alkyl with 1–5 C atoms and m being 1–7.

Preferably, R¹ is a vinyl ether group, an acrylate group, an amino group or a mercapto group, and especially preferred are the following meanings of R¹:

CH₂=CH—COO—    R¹-1

CH₂=C—COO—    R¹-2
      |
      CH₃

CH₂=C—COO—    R¹-3
      |
      Cl

CH₂=CH—O—    R¹-4

H₂N—    R¹-5

H(alkyl)N—    R¹-6

HS—CH₂—(CH₂)ₘ—COO—    R¹-7

    R¹-8 with alkyl denoting C₁–C₃-alkyl and m being 1–5.

In the compounds of formulae Ia–Iq, the spacer-type group P is alkylene with up to 12 C atoms, preferably with 2 to 10, in particular with 2 to 6, it also being possible for one or more non adjacent CH₂ groups to be replaced by O.

In case P is alkylene, P may be straight-chain or branched. P especially preferred is ethylene, propylene, butylene, 1-methyl-propylene, 2-methyl-propylene, pentylene, 1-methyl-butylene, 2-methyl-butylene, hexylene, 2-ethyl-butylene, 1,3-dimethyl-butylene, heptylene, 1-methylhexylene, 2-methylhexylene, 3-methylhexylene, 4-methylhexylene, 5-methylhexylene, 6-methylhexylene, octylene, 3-ethyl-hexylene, nonylene, 1-methyl-octylene, 2-methyloctylene, 7-methyloctylene, decylene, undecylene, dodecylene, 2-methylundecylene, 2,7,5-trimethyl-nonylene or 3-propyl-nonylene.

In case P is mono- or polyoxaalkylene, P may be straight-chain or branched. In particular, P is 1-oxa-ethylene, 1-oxa-propylene, 2-oxapropylene, 1-oxa-butylene, 2-oxabutylene, 1,3-dioxabutylene, 1-oxa-pentylene, 2-oxa-pentylene, 3-oxy-pentylene, 2-oxa-3-methyl-butylene, 1-oxahexylene, 2-oxa-hexylene, 3-oxa-hexylene, 1,3-dioxa-hexylene, 1,4-dioxy-hexylene, 1,5-dioxa-hexylene, 1-oxy-heptylene, 2-oxa-heptylene, 1,3-dioxa-heptylene, 1,4-dioxa-heptylene, 1,5-dioxa-heptylene, 1,6-dioxa-heptylene, 1,3,5-trioxa-heptylene, 1-oxa-octylene, 2-oxa-octylene, 3-oxa-octylene, 4-oxa-octylene, 1,3-dioxa-octylene, 1,4-dioxa-nonylene, 1,4-dioxa-decylene, 1,4-dioxa-undecylene and 1,3,5-trioxa-dodecylene.

The inventive materials comprising compounds with short-chained and long-chained spacers have reduced tendency to form smectic phases. The term short-chained spacer denotes a spacer with 2 to 5 C atoms and the term long-chained spacer denotes a spacer with 6 to 15 C atoms. The short-chained spacer exhibits as a rule 2 to 8 C atoms less than the long-chained spacer.

X is —O—, —S—, —COO—, —OCO— or a single bond and in particular —O—, —COO—, —OCC— or a single bond. In case X is —O—, —S— or —OCO—, the adjacent CH₂— group of Q is not replaced by —O—.

Z is preferably —COO—, —OCO—, —CH₂CH₂— or a single bond, in particular —CO—O— or a single bond.

R³ can be an alkyl radical with up to 15 C atoms which is unsubstituted, mono or polysubstituted by halogen, it also being possible for one or more CH₂ groups in these radicals to be replaced, in each case independently from one another, by —O—, —S—, —CO—, —OCO—, —COO— or —O—COO— in such a manner that oxygen atoms are not linked directly to one another.

If R³ and/or R⁶ are each independently an alkyl radical or alkoxy radical, it may be straight-chain or branched. Preferably, it is straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy or octoxy, and furthermore methyl, nonyl, decyl, undecyl, tridecyl, tetradecyl, pentadecyl, methoxy, nonoxy, decoxy, undecoxy, dodecoxy, tridecoxy or tetradecoxy.

If $R^3$ and/or $R^6$ are each independently oxaalkyl, it is preferably straight-chain 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7-or 8-oxanonyl, 2-, 3-, 4-, 5-, 6-, 7-, 8-, or 9-oxadecyl.

The compounds of formula I are partly novel and partly known, for example from EP 0 399 279.

But these docurnments deal with ferroelectric liquid crystalline polymers.

There is no hint to materials in which the polymerized material forms a network or to bifunctional reactive chiral compounds nor to chiral vinylether derivatives.

The inventive compounds can be prepared from the commercially available terpenols according to the following reaction scheme:

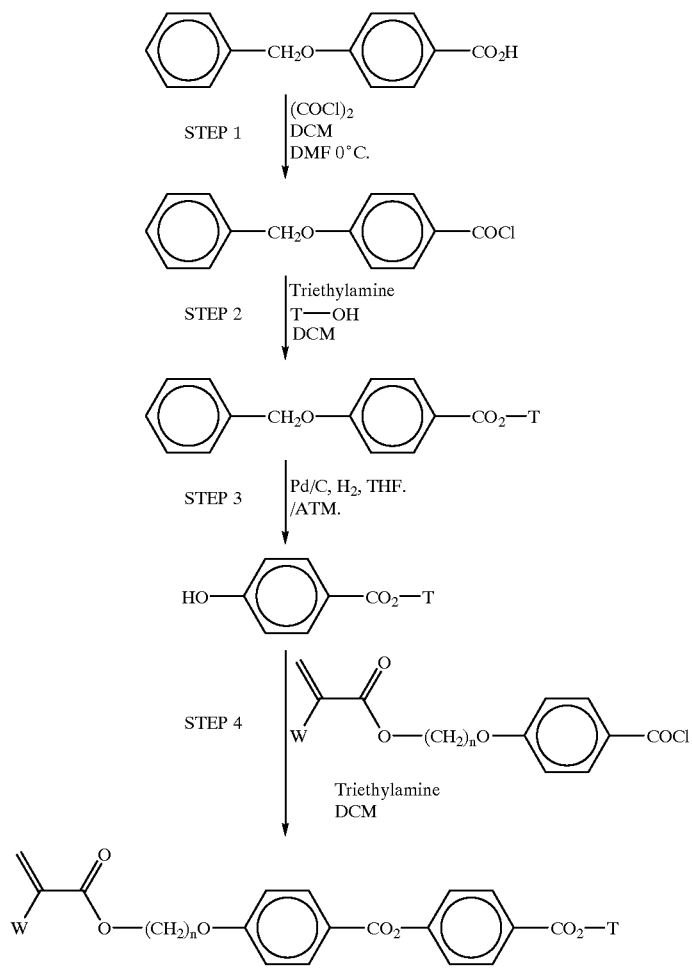

The inventive display exhibits two opposite plates which are transparent to light and which will hereinafter be termed substrates. Optionally on the substrate there is provided an orientation layer of, for example, rubbed polyimide or polyamide by means of which the liquid crystalline material according to the invention can be homogeneously aligned between the substrate.

The liquid crystalline material can be capillary filled between two substrates which are provided with aligning layers, and is then subsequently cured, for example, by irradiation with UV light, preferably in the presence of a photoinitiator, for example, an Irgacure®.

Another attractive technique comprises coating of the LC material on a substrate with subsequent curing. The film may be peeled off and arranged on other substrates if required.

The color being dependent on the pitch length of the cholesteric helix according to the equation $\lambda_{max} = \bar{n} \, P \cos \Theta$ $\bar{n}$=mean refractive index of the LC, P=pitch length
$\Theta$=viewing angle from normal incidence.

The pitch length obtained when adding a chiral dopant to a nematic host depends on the polarizing ability of the LC molecules—the more polarizable they are the tighter the pitch length obtained (higher twisting power), so using a non-polar host may significantly alter how much chiral dopant would be needed to produce a given color.

Also films reflecting infra red light can be made.

In all these cases the waveband of light reflected is given by $\Delta\lambda = \Delta nP$, typically $\Delta n = 0.13-0.15$, the reflected light being circularly polarized with the same 'sense' as that of the helix of the cholesteric phase. Only 50% of the light in the aforementioned waveband is reflected, the rest is transmitted with a helical sense of opposite sign. This can, in turn, be reflected by a second identical film but of opposite helical sense placed behind the first film. In this way all the waveband can be reflected.

These films can be made either flexible or brittle depending on crosslinking. The brittle films can be 'flaked' and the flakes used as a 'pigment' in a variety of inks or paints for use in cosmetics (nail varnish) or car paint. Flexible film can be made into optical coatings which reflect some light, e.g. infra red coatings on windows.

The novel chiral reactive liquid crystalline compounds and compositions are highly suitable to produce cholesteric films which can be used in different optical and electrooptical applications.

Furthermore, they are useful as colored films for decorative applications.

The invention will be explained in more detail by means of the following examples of the preparation of a liquid crystalline material according to the invention.

The mesogenic phases are abbreviated as following:

| K | crystalline |
| N | nematic |
| S | smectic |
| BP | blue phase |
| N* | chiral nematic (cholesteric) | is prepared via the sequence of reaction steps shown in Scheme 1.

In step 2 of Scheme 1, 1 mol of (+)-menthol and 1.1 mol of benzoyl chloride obtained in step 1 are dissolved in 1 l of dichloromethan(DCM). 1.1 mol of triethylamine are added, and the mixture is stirred for 3 hours at room temperature. After reductive cleavage of the benzyl group in step 3, the phenol is esterified in step 4. The product shows K42 I.

Analogously are obtained:

EXAMPLE 1

The chiral reactive liquid crystalline compound (1)

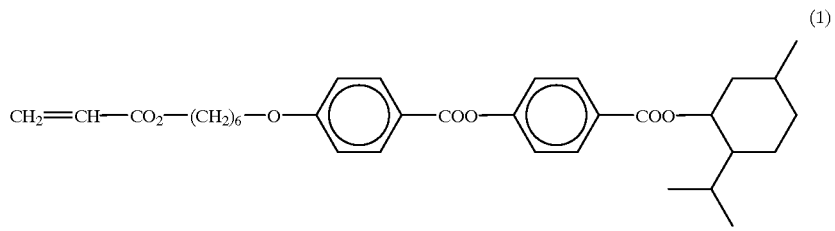

(1)

| T* | s | n |
|---|---|---|
| $CH_2{=}CH{-}CO{-}O{-}(CH_2)_n{-}O{-}\bigcirc{-}COO{\rightarrow}_s\bigcirc{-}COO{-}T^*$ | | |
| (+)ment | 1 | 4 |
| (+)ment | 1 | 2 |
| (−)ment | 1 | 6 |
| (−)ment | 1 | 4 |
| (−)ment | 1 | 2 |
| (+)ment | 0 | 6 |
| (+)ment | 0 | 4 |
| (+)ment | 0 | 2 |
| (−)ment | 0 | 6 |
| ipc | 1 | 6 |
| ipc | 0 | 6 |
| cit | 1 | 6 |
| cit | 0 | 6 |

-continued

| T* | s | n |
|---|---|---|

CH₂=CH—O—(CH₂)ₙ—O—⟨⟩—COO—⟨⟩ₛ—⟨⟩—COO—T*

| | | |
|---|---|---|
| (+)ment | 0 | 6 |
| (−)ment | 1 | 6 |
| (−)ment | 1 | 4 |
| (+)ment | 0 | 2 |

CH₂=CH—COO—(CH₂)ₙ—O—⟨⟩—COO—⟨⟩ₛ—⟨⟩—COO—T*

| | | |
|---|---|---|
| (+)ment | 1 | 6 |
| (+)ment | 1 | 4 |
| (+)ment | 1 | 2 |
| (+)ment | 0 | 6 - oil |
| (+)ment | = (1S, 2R, 5S)-(+)-menthyl | |
| (−)ment | = (1R, 2S, 5R)-(−)-menthyl | |
| ipc | = isopinocamphexyl | |
| cit | = citronellyl | |

CH₂=CHCO₂(CH₂)₆O—⟨⟩—⟨⟩—COO—[menthyl]  K681

EXAMPLE 2

A mixture is formulated consisting of

H₂C=CH·CO·O—(CH₂)₆—O—⟨⟩—⟨⟩—CO·O—[menthyl]    13%

H₂C=C(CH₃)—CO·O—(CH₂)₆—O—⟨⟩—CO·O—⟨⟩—O—CO—⟨⟩—O—(CH₂)₆—O—CO·C(CH₃)=CH₂    86%

IRGACURE 651    1%

It forms a cholesteric layer which reflects red light.

The resulting mixture is photo-polymerized to achieve full polymerisation and to give a chiral polymeric network.

We claim:

1. A liquid crystalline material in the form of a cholesteric polymer network having polymerized terpenoid units therein, wherein the material is obtained by copolymerization of a compound (a) having at least two polymerizable functional groups and a chiral polymerizable terpenoid-containing compound (b) of the formula I $$R^1\text{-}(P)_u\text{-}X\text{-}(MG^1\text{-}COO)_s\text{-}T \qquad I$$

wherein

T is a terpenoid radical, $R^1$ $CH_2=CW-COO-$,

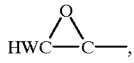

$HWN-$, $CH_2=CH-$, $CH_2=CH-O-$ or $HS-CH_2-(CH_2)_m-COO-$ with W being H, Cl or alkyl with 1–5 C atoms and m being 1–7, P is alkylene with 1 to 12 C atoms, one or more non-adjacent CH₂ groups optionally being replaced by —O—, X is —O—, —S—, —COO—, —OCO— or a single bond, MG$^1$ is an aromatic ring system or a mesogenic group, selected from groups of the following formulae:

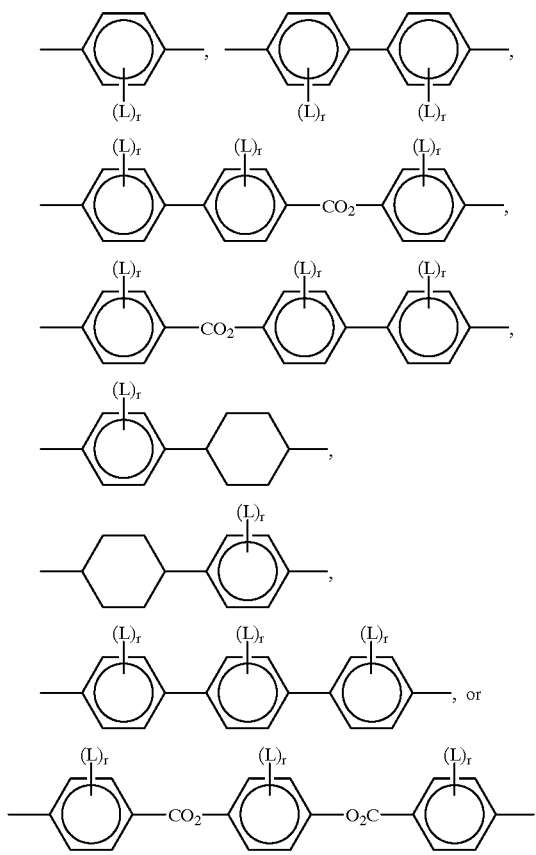

with L being CH$_3$, —COCH$_3$, —CN, F or Cl and r being 0, 1 or 2,

-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-subsituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$—, —CH$_2$CH$_2$—, —C≡C— or a single bond s is 0 or 1, and u is or 1.

2. A liquid crystalline material of claim 1, wherein the terpenoid-containing compound (b) contains a terpenoid radical selected from menthyl, neomenthyl, isopinocampheyl, isolongifolyl, fenchyl, corveyl, myrthenyl, nopyl, citronelly or dihydrocitronellyl.

3. A liquid crystalline material of claim 1, wherein the compound (a) is a bisacrylate of formula IIa

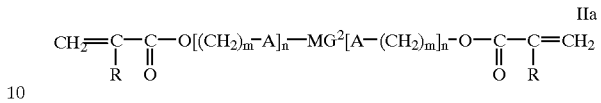

wherein

R is H, CH$_3$ or Cl,

A is —O—, —CO—O—, —O—CO— or a single bond, n and m are integers from 0 to 20, and MG$^2$ has the meaning given for MG$^1$.

4. A liquid crystalline material of claim 3, wherein MG$^2$ is selected from:

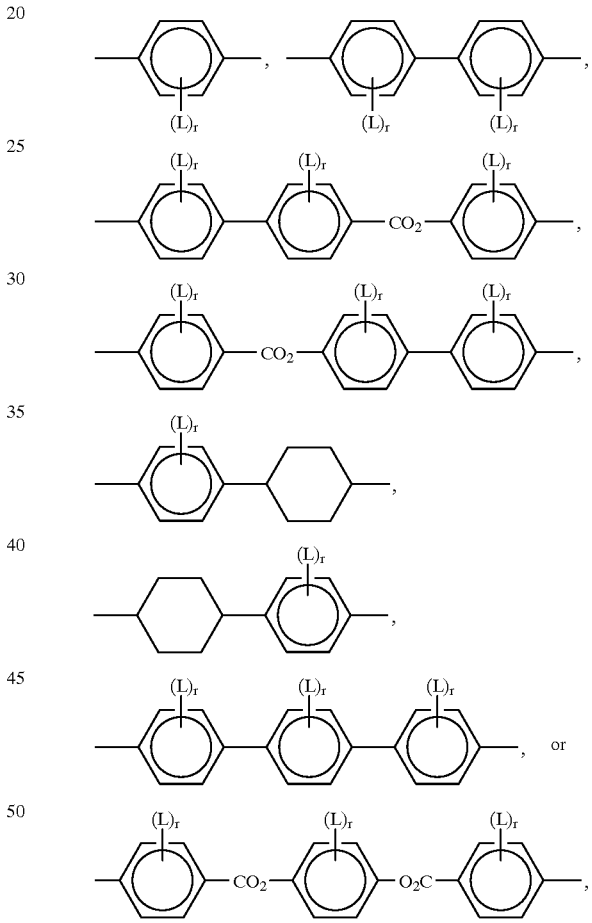

with L being CH$_3$, —COCH$_3$, —CN, F or Cl and r being 0, 1 or 2.

5. A liquid crystalline material according to claim 1, wherein the liquid crystalline material comprises a unit obtained by copolymerization of at least one achiral compound having one polymerizable functional group.

6. A liquid crystalline material according to claim 4, wherein the achiral compound having one polymerizable group is a compound of formula III R$^2$-(P)$_u$-X-MG$^3$-R$^3$     III in which $R^2$ CH$_2$=CW—COO—,

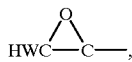

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$ groups optionally being replaced by —O—, X is —O—, —S—, —COO—, —OCO— or a single bond, MG$^3$ is an aromatic ring system or a mesogenic group selected from groups of the following formulae:

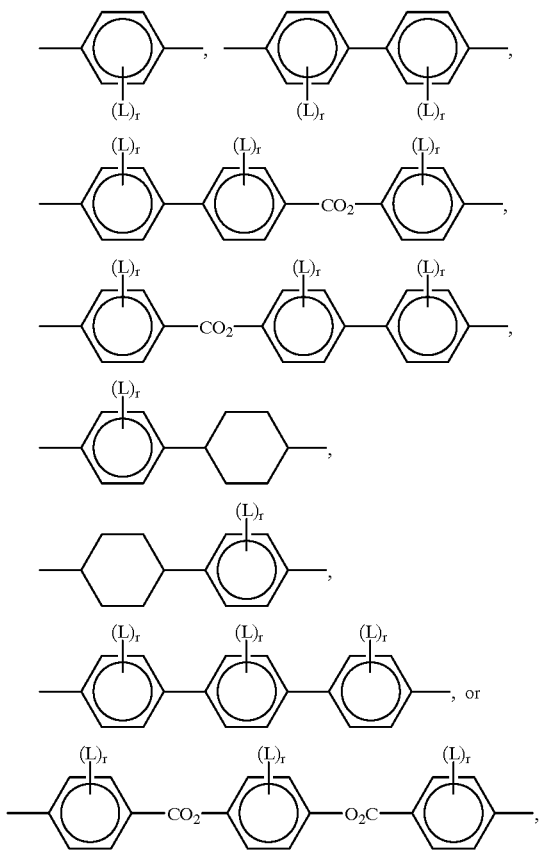

with L being CH$_3$, —COCH$_3$, —CN, F or Cl and r being 0, 1 or 2,

-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-subsituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$—, —CH$_2$CH$_2$—, —C≡C— or a single bond u is 0 or 1, and R$^3$ is an optionally halogenated alkyl radical with 1 to 15 C atoms, one or more CH$_2$ groups in these radicals optionally being replaced by —O—, —S—, —SO—, —OC—, —COO— or —O—CO—O in such a manner that oxygen atoms are not linked directly to one another.

7. A liquid crystalline material of claim 6, which contains at least one compound of the formula III wherein u is 1 and P is alkylene of 2 to 5 carbon atoms, one or more non-adjacent CH$_2$ groups optionally being replaced by —O—, and at least one compound of the formula III wherein u is 1 and P is alkylene of 6 to 15 carbon atoms, one or more non-adjacent CH$_2$ groups optionally being replaced by —O—.

8. The liquid crystalline material of claim 1, which is in the form of a film of the polymer network on a substrate.

9. The liquid crystalline material in the form of a film of claim 8, wherein the film reflects infrared light.

10. A polymer network film prepared by coating and curing a liquid crystalline material according to claim 1 on a substrate, optionally peeling the film off the substrate and optionally applying the film to a different substrate.

11. A polymer network film of claim 10 that reflects circularly polarized light with the same sense as that of the helix of the cholesteric phase.

12. A polymer network film of claim 10 which reflects infrared light.

13. A polymer network film of claim 10 which is a flexible film.

14. A polymer network film of claim 10 which is a brittle film.

15. A copolymerizable precursor material comprising at least one bifunctional reactive achiral compound of formula II

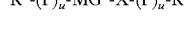   II where

R$^4$ is CH$_2$=CW—COO—,

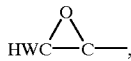

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$ groups optionally being replaced by —O—, X is —O—, —S—, —COO—, —OCO— or a single bond, MG$^2$ is an aromatic ring system or a mesogenic group selected from the groups of the following formulae:

with L being CH$_3$, —COCH$_3$, —CN, F or Cl and r being 0, 1 or 2,
-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-subsituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$—, —CH$_2$CH$_2$—, —C≡C— or a single bond and u is 0 or 1, and at least one chiral polymerizable terpenoid-containing compound of the formula I $$R^1\text{-}(P)_u\text{-}X\text{-}(MG^1\text{---}COO)_sT \qquad I$$

wherein

T is a terpenoid radical,

R$^1$ is CH$_2$=CW—COO—,

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$groups optionally being replaced by —O—, X is —O—, —S—, —COO—, —OCO— or a single bond, MG$^1$ is an aromatic ring system or a mesogenic group selected from the groups of the following formulae:

with L being CH$_3$, —COCH$_3$, —CN, F or Cl and r being 0, 1 or 2,
-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe'-
-Phe'-Z-Phe"-Pyd-
-Phe'-Z-Phe"-Pyr- -Nap'-Z-Phe"-Phe"-

-Nap'-Z-Phe'-Pyrwherein Phe is 1,4-phenylene, which is unsubstituted or mono- to poly-substituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$, —CH$_2$CH$_2$—, —C≡C— or a single bond.

s is 0 or 1, and u is 0 or 1.

16. A copolymerizable precursor material according to claim 15, wherein R$^1$ in formula I and R$^4$ in formula II are independently acrylate radicals of the formula

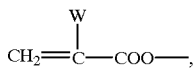

wherein

W is H, Cl or alkyl of 1–5 C aotms.

17. A copolymerizable precursor material according to claim 15, wherein R$^1$ in formula I and R$^4$ in formula II are vinylether radicals of the formula CH$_2$=CH—O—.

18. A copolymerizable precursor material comprising at least one chiral polymerizable compound of formula I R$^1$-(P)$_u$-X-(MG$^1$—COO)$_s$T      I wherein T is a terpenoid radical, R$^1$ is CH$_2$=CW—COO—,

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$ groups optionally being replaced by —O—, X is —O—, —S—, —COO—, —OCO— or a single bond, MG$^1$ is an aromatic ring system or a mesogenic group selected from the groups of the following formulae:

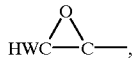

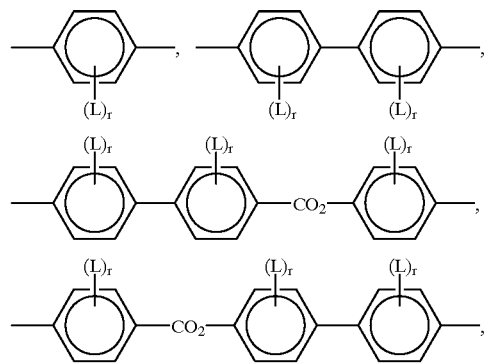

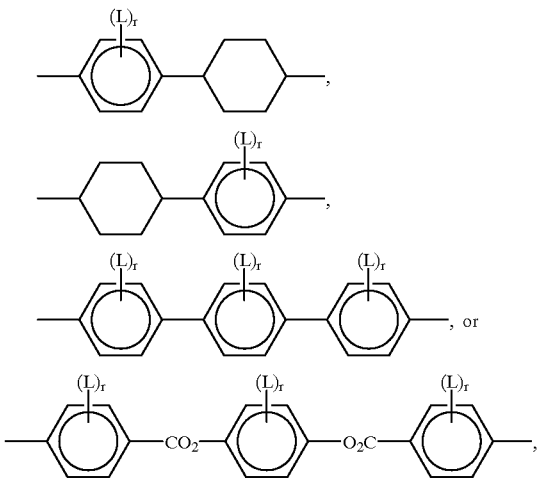

with L being CH$_3$, —COCH$_3$, —CN, F or Cl and r being 0, 1 or 2,

-Phe'-Z-Phe-

-Phe'-Z-Pyd-

-Phe'-Z-Pyr-

-Nap'-Z-Phe'-

-Nap-Z-Pyd-

-Nap-Z-Pyr-

-Phe'-Z-Phe"-Phe"-

-Phe'-Z-Pyd-Phe"-

-Phe'-Z-Pyr-Phe"-

-Phe'-Z-Phe"-Pyd-

-Phe'-Z-Phe"-Pyr-

-Nap'-Z-Phe"-Phe"-

-Nap'-Z-Phe'-Pyrwherein Phe is 1,4-phenylene, which is unsubstituted or mono- to poly-substituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$, —CH$_2$CH$_2$—, —C≡C— or a single bond.

s is 0 or 1, and u is 0 or 1, and at least two achiral polymerizable compounds of formula III R$^2$-(P)$_u$-X-MG$^3$-R$^3$      III in which R$^2$ is CH$_2$=CW—COO—,

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$ groups optionally being replaced by —O—, X is —O—, —S—, —COO—, —OCO—or a single bond, MG³ is an aromatic ring system or a mesogenic group selected from groups of the following formulae:

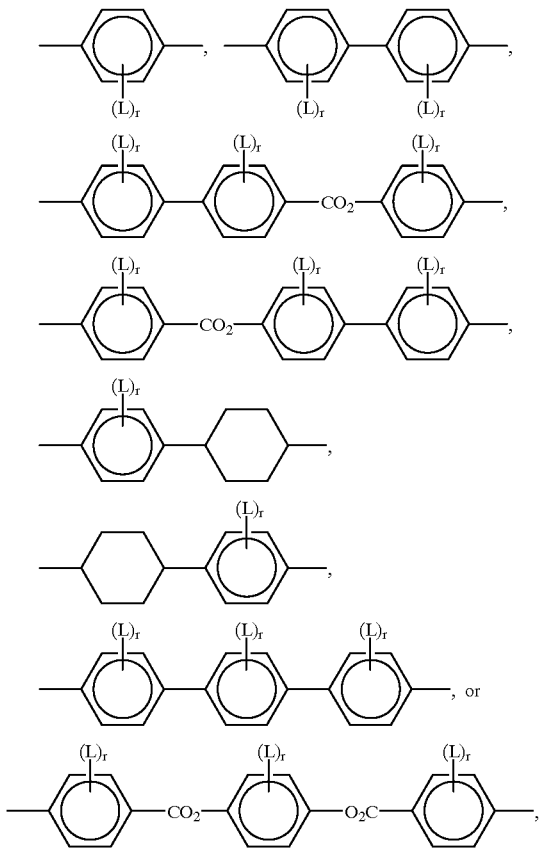

with L being CH₃, —COCH₃, —CN, F or Cl and r being 0, 1 or 2,
-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-subsituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH₂O—, —OCH₂—, —CH₂CH₂—, —C≡C— or a single bond u is 0 or 1, and R³ is an optionally halogenated alkyl radical with 1 to 15 C atoms, one or more CH₂ groups in these radicals optionally being replaced by —O—, —S—, —SO—, —OCO—, —COO— or —O—CO—O— in such a manner that oxygen atoms are not linked directly to one another, which contains at least one compound of the formula III wherein u is 1 and P is alkylene of 2 to 5 C atoms, one or more non-adjacent CH₂ groups optionally being replaced by —O—, and at least one compound of the formula III wherein u is 1 and P is alkylene of 6 to 15 C atoms, one or more non-adjacent CH₂ groups optionally being replaced by —O—.

19. A copolymerizable precursor material comprising at least one chiral compound of formula I

R¹-(P)ᵤ-X-(MG¹—COO)ₛT        I wherein

T is a terpenoid radical,

R¹ is CH₂=CW—COO—,

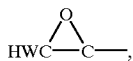

HWN—, CH₂=CH—, CH₂=CH—O— or HS—CH₂—(CH₂)ₘ—COO— with W being H, Cl or alkyl with 1–5 C atoms and m being 1–7, P is alkylene with 1 to 12 C atoms, one or more non-adjacent CH₂ groups optionally being replaced by —O—, X is —O—, —S—, —COO—, —OCO— or a single bond, MG¹ is an aromatic ring system or a mesogenic group selected from the groups of the following formulae:

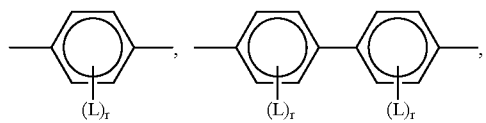

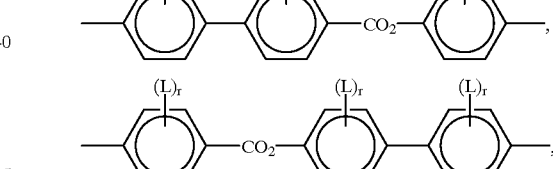

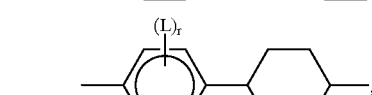

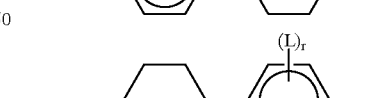

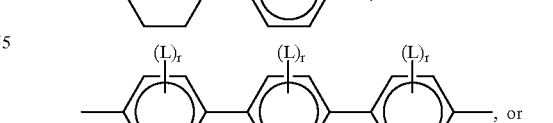

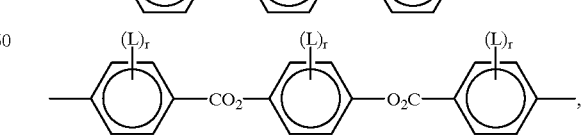

with L being CH₃, —COCH₃, —CN, F or Cl and r being 0, 1 or 2,

-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-substituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$, —CH$_2$CH$_2$—, —C≡C— or a single bond.

s is 0 or 1, and u is 0 or 1, and at least one achiral polymerizable compound of formula IV

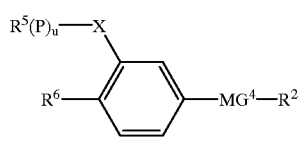

IV wherein P, X and u have the meaning given,

MG$^4$ has the meaning given for MG$^1$, and

R$^2$, R$^5$ and R$^1$ have the meaning given for R$^1$.

20. A reactive chiral compound of formula I $R^1$-(P)$_u$-X-(MG$^1$—COO)$_s$T      I wherein T is a terpenoid radical, R$^1$ is CH$_2$=CW—COO—,

HWN—, CH$_2$=CH—, CH$_2$=CH—O— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$groups optionally being replaced by —O—, X is —O—, —S—, —COO—, —OCO— or a single bond, MG$^1$ is an aromatic ring system or a mesogenic group selected from the groups of the following formulae:

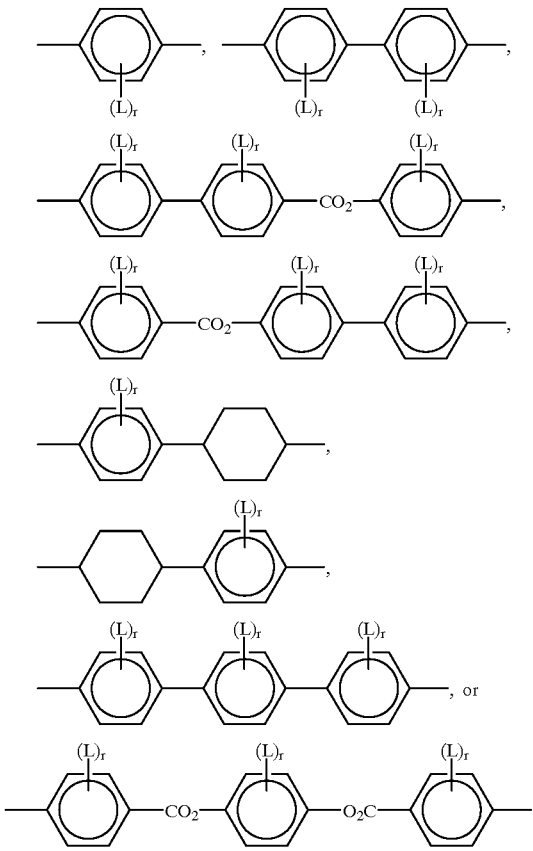

with L being CH$_3$, —COCH$_3$, —CN, F or Cl and r being 0, 1 or 2,

-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-substituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH$_2$O—, —OCH$_2$, —CH$_2$CH$_2$—, —C≡C— or a single bond.

s is 0 or 1, and u is 0 or 1, having at least one aromatic ring substituted by fluorine.

21. A reactive chiral compound of formula I

      I in which

T is a terpenoid radical, $R^1$ is $CH_2$=CH—$CO_2$—,

P is a spacer of formula —$(CH_2)_k$— with k being an integer between 2 and 10,

X is —O—, $MG^1$ is an aromatic ring system or a mesogenic group selected from the groups of the following formulae:

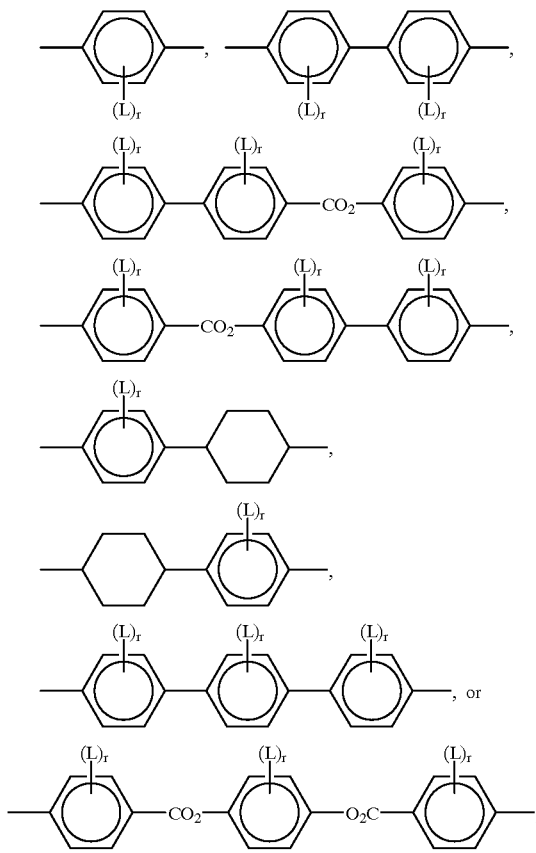

with L being $CH_3$, —$COCH_3$, —CN, F or Cl and r being 0, 1 or 2,

-Phe'-Z-Phe-
-Phe'-Z-Pyd-
-Phe'-Z-Pyr-
-Nap'-Z-Phe'-
-Nap-Z-Pyd-
-Nap-Z-Pyr-
-Phe'-Z-Phe"-Phe"-
-Phe'-Z-Pyd-Phe"-
-Phe'-Z-Pyr-Phe"-
-Phe'-Z-Phe"-Pyd-
-Phe'-Z-Phe"-Pyr-
-Nap'-Z-Phe"-Phe"-
-Nap'-Z-Phe'-Pyrwherein Phe is 1,4-phenylene, which is unsubstituted or mono- to poly-substituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —$CH_2$O—, —O$CH_2$, —$CH_2CH_2$—, —C≡C— or a single bond.

s is 0 or 1, and u is 0 or 1.

22. A reactive chiral compound of formula I1

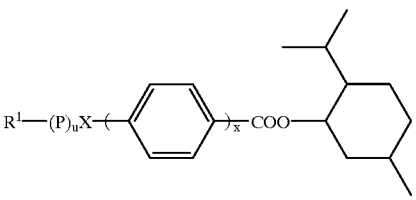

in which $R^1$ is $CH_2$=CW—COO—,

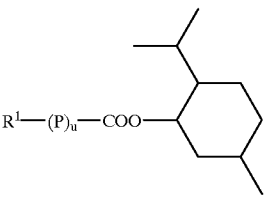

HWN—, $CH_2$=CH—, $CH_2$=CH—O— or HS—$CH_2$—$(CH_2)_m$—COO— with W being H, Cl or alkyl with 1–5 C atoms and m being 1–7, P is alkylene with 1 to 12 C atoms, one or more non-adjacent $CH_2$ groups optionally being replaced by —O—, X is —O—, —S—, —COO—, —OCO—or a single bond, u is 0 or 1, and x is 1, 2 or 3.

23. A reactive chiral compound of formula I2

I2

$R^1$—$(P)_u$—COO— in which $R^1$ is $CH_2$=CW—COO—,

HWC—C—,

HWN—, $CH_2$=CH—, $CH_2$=CH—O— or HS—$CH_2$—$(CH_2)_m$—COO— with W being H, Cl or alkyl with 1–5 C atoms and m being 1–7, P is alkylene with 1 to 12 C atoms, one or more non-adjacent $CH_2$ groups optionally being replaced by —O—, and u is 0 or 1.

24. An achiral polymerizable compound of formula IV

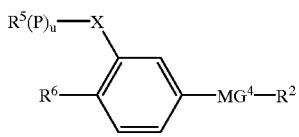

IV in which

R⁵ is CH₂=CW—COO—,

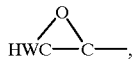

HWN—, CH₂=CH—, CH₂=CH—O— or HS—CH₂—(CH₂)ₘ—COO— with W being H, Cl or alkyl with 1–5 C atoms and m being 1–7, P is alkylene with 1 to 12 C atoms, one or more non-adjacent CH₂ groups optionally being replaced by —O—, X is —O—, —S—, —COO—, —OCO—or a single bond, MG⁴ is an aromatic ring system or a mesogenic group selected from groups of the following formulae:

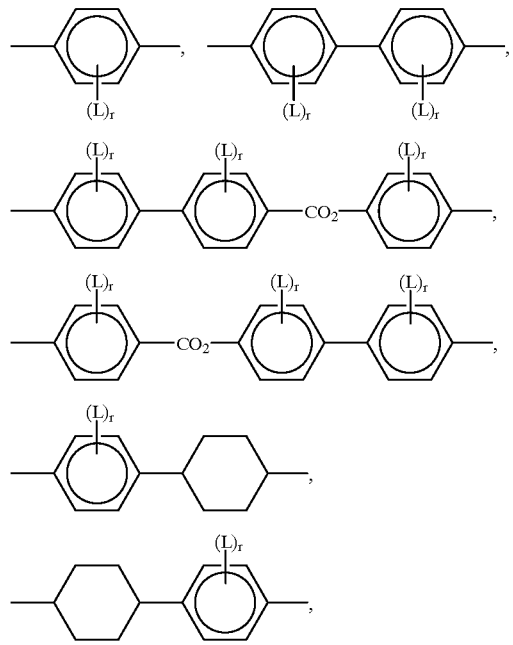

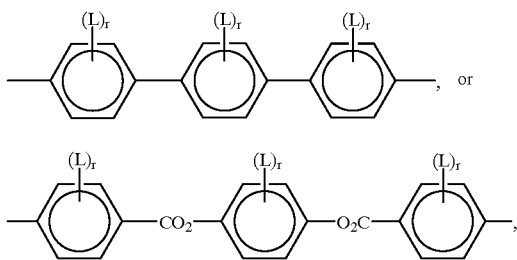

with L being CH₃ —COCH₃, —CN, F or Cl and r being 0, 1 or 2,

-Phe'-Z-Phe-

-Phe'-Z-Pyd-

-Phe'-Z-Pyr-

-Nap'-Z-Phe'-

-Nap-Z-Pyd-

-Nap-Z-Pyr-

-Phe'-Z-Phe "-Phe"-

-Phe'-Z-Pyd-Phe"-

-Phe'-Z-Pyr-Phe"-

-Phe '-Z-Phe "-Pyd-

-Phe'-Z-Phe"-Pyr-

-Nap'-Z-Phe"-Phe"-

-Nap'-Z-Phe'-Pyrwherein Phe is 1,4-phenylene, which is unsubstituted or mono- to poly-substituted by CN or halogen, Nap is a naphthaline-2,6-diyl which is unsubstituted or substituted 1–4 times by halogen, Pyd denotes pyrimidine-2,5-diyl, Pyr denotes pyridine-2,5-diyl, and Z denotes —CO—O—, —O—CO—, —CH₂O—, —OCH₂—, —CH₂CH₂—, —C≡C— or a single bond u is 0 or 1, and R² and R⁶, independently, are an optionally halogenated alkyl radical with 1 to 15 C atoms, one or more CH₂ groups in these radicals optionally being replaced by —O—, —S—, —SO—, —OCO—, —COO—or —O—CO—O— in such a manner that oxygen atoms are not linked directly to one another.

\* \* \* \* \*